United States Patent [19]

Holtkamp, Sr.

[11] Patent Number: Plant 7,677

[45] Date of Patent: Oct. 15, 1991

[54] AFRICAN VIOLET PLANT NAMED GRENADA

[76] Inventor: Reinhold Holtkamp, Sr., Blumenstrasse 28, D 4242 Rees-Haffen, Fed. Rep. of Germany

[21] Appl. No.: 551,739

[22] Filed: Jul. 12, 1990

[51] Int. Cl.[5] ..... A01H 5/00

[52] U.S. Cl. ..... Plt./69

[58] Field of Search ..... Plt./69

[56] References Cited

U.S. PATENT DOCUMENTS

P.P. 6,525 1/1989 Holtkamp ..... Plt. 69

*Primary Examiner*—James R. Feyrer

*Attorney, Agent, or Firm*—Foley & Lardner

[57] ABSTRACT

A new and distinct cultivar of African violet named Grenada characterized by its single violet-shaped, light blue flowers with white, slightly frilled edges and darker center; strong, upright flower stems that curve slightly toward the center to form a compact bouquet above the leaves; medium green, oval to heart-shaped, leaves; profuse flowering, vigorous growth habit, flowering 10–11 weeks after potting, and its long lasting and non-dropping flowers.

1 Drawing Sheet

The present invention comprises a new and distinct cultivar of African violet plant, botanically known as *Saintpaulia ionantha,* and hereinafter referred to by the cultivar name Grenada.

The new cultivar was referred to during the breeding and selection process by the designation H 5/1/83 and is a product of a planned breeding program. The new cultivar was originated from a cross made by me in the controlled breeding program in Haffen, Federal Republic of Germany. The female, or seed parent was a cultivar designated 450/84. The male, or pollen parent was a cultivar designated 620/3.

Grenada was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Grenada has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Grenada, which in combination distinguish this African violet as a new and distinct cultivar:

(1) Strong, upright flower stems curving slightly toward the center.

(2) Light blue flowers with slightly frilled white edges.

(3) Profuse flowering.

(4) Each plant carries 10–12 and more upright flower stems each of which carries 8–12 and more flowers.

(5) Long lasting, non-dropping flowers.

(6) Vigorous grower.

(7) Plant saleable 10 to 11 weeks after potting.

(8) Seed capsules push slightly through.

(9) Medium green, oval to heart-shaped leaves.

(10) After maturity the flowers dry off, and remain on the peduncle without becoming infected by botrytis.

Grenada is similar in certain respects to Molokai, disclosed in U.S. Plant Pat. No. 6,525. The light blue blooms with white edges of Molokai and Grenada are in the same general category. However, the petals of Molokai are noticeably darker (91A-B), with the center of Molokai (90A-B) also being considerably darker than the center of Grenada. Grenada is also distinguished by its leaf shape and color.

The accompanying color photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Grenada.

Parentage:

*Male parent.*—450/84.

*Female parent.*—620/3.

Propagation: The new cultivar holds its distinguishing characteristics through successive propagations by leaf cuttings.

Plant: From 9 cm to 11 cm tall when grown in pots, and approximately 24–28 cm in diameter when fully grown.

Leaves:

*General form.*—Oval to heart-shaped.

*Diameter.*—60–65 mm wide and 65–70 mm long.

*Texture.*—Leather-like.

*Aspect.*—Hairy, slightly shiny.

*Veins.*—Upperside: well visible; underside: well pronounced, light green, shiny.

*Color (upperside).*—Yellow-Green Group 147 A.

*Color (underside).*—Greyed-Purple Group 186 B to C.

*Petiole.*—Strong upright, green with purplish-red touch, hairy.

Flowers:

*Buds.*—Round-shaped, light green and blue, 7–8 mm just before opening.

*Sepals.*—Five (5). Color: Purplish-brown.

*Calyx.*—Shape: Funnel-shaped. Aspect: Spear-shaped, hairy.

*Peduncle.*—Character: Strong upright, hairy. Color: Purplish-brown.

Individual flowers:

*Size.*—35–40 mm.

*Shape.*—Single violet-shaped with slightly frilled edges

*Color* (*upperside*).—Violet-Blue Group 92 C with white edges, center between 92 B and A. Under cooler temperatures and more intensive lighting, the blue color tends to intensify.

*Color* (*underside*).—Violet-Blue Group 92 C to D.

*Borne.*—Each flower stem carries 8–12 and more flowers on strong, upright peduncle that are free standing above the leaves, thereby forming a compact bouquet.

*Flowering habit.*—Flowers 10–11 weeks after potting.

Reproductive organs:

*Stamens.*—Two (2). Anthers: 2 composed of 4 anther cells, seed capsule pushes slightly through.

*Filaments.*—Yellowish green with blue on edges, 3–4 mm long.

*Pollen color.*—Yellow Group 7 A.

*Styles.*—7–8 mm long, purplish blue, base of ovary light green and hairy.

Roots: Normally developed, white when young, turning slightly brownish when older.

Disease resistance: Good.

General observations: Grenada is an attractive, vigorous grower with medium green, oval to heart-shaped leaves. A tight bouquet of single violet-shaped flowers free standing above the leaves develops after approximately 10–11 weeks. Each of the 10–12 and more strong flower stems carries 8–12 and more light blue flowers with white, slightly frilled edges and darker center. Occasionally, one to two additional small petals may develop in the center. The flowers are long-lasting and non-dropping and the seed capsules push slightly through.

I claim:

1. A new and distinct cultivar of African violet named Grenada, as described and illustrated, and particularly characterized by its single violet-shaped, light blue flowers with white, slightly frilled edges and darker center; strong, upright flower stems that curve slightly toward the center to form a compact bouquet above the leaves; medium green, oval to heart-shaped, leaves; profuse flowering, vigorous growth habit, flowering 10–11 weeks after potting, and its long lasting and non-dropping flowers.

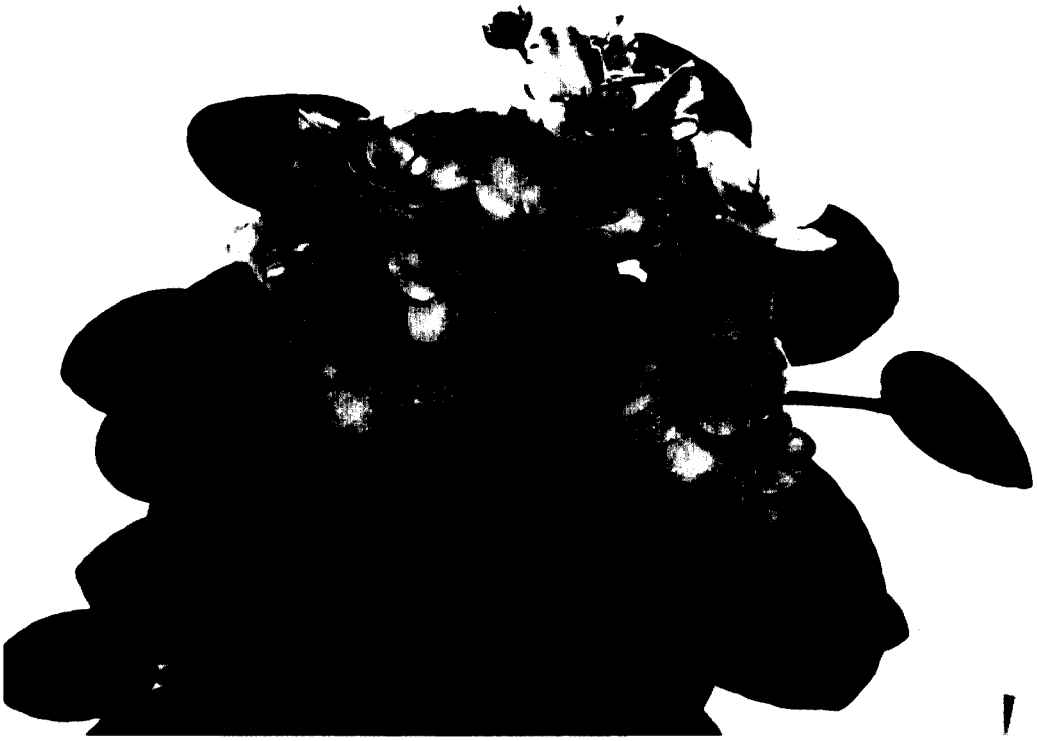

* * * * *